(12) United States Patent
Potyrailo et al.

(10) Patent No.: US 6,881,585 B1
(45) Date of Patent: Apr. 19, 2005

(54) METHOD AND APPARATUS FOR RAPID SCREENING OF VOLATILES

(75) Inventors: Radislav Alexandrovich Potyrailo, Niskayuna, NY (US); James Claude Carnahan, Niskayuna, NY (US); Ralph Joseph May, Niskayuna, NY (US); John Patrick Lemmon, Delanson, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/519,330

(22) Filed: Mar. 6, 2000

(51) Int. Cl.[7] ............................................ G01N 27/416
(52) U.S. Cl. ...................... 436/151; 73/1.02; 73/19.01; 73/19.1; 73/24.04; 73/335.01; 73/61.77; 73/863.21
(58) Field of Search .......................... 436/151; 73/1.02, 73/19.01, 19.1, 24.04, 335.01, 61.77, 863.21

(56) References Cited

U.S. PATENT DOCUMENTS

| | | | |
|---|---|---|---|
| 4,759,210 A | | 7/1988 | Wohltjen |
| 4,781,798 A | * | 11/1988 | Gough .................. 204/403.13 |
| 4,818,348 A | | 4/1989 | Stetter |
| 4,888,295 A | | 12/1989 | Zaromb et al. |
| 5,076,094 A | | 12/1991 | Frye et al. |
| 5,191,786 A | | 3/1993 | Baughman et al. |
| 5,233,194 A | * | 8/1993 | Mauze et al. ............ 250/341.2 |
| 5,235,843 A | | 8/1993 | Langhorst |
| 5,289,715 A | | 3/1994 | Staples et al. |
| 5,320,814 A | | 6/1994 | Walt et al. |
| 5,345,213 A | | 9/1994 | Semancik et al. |
| 5,411,709 A | | 5/1995 | Furuki et al. |
| 5,442,169 A | * | 8/1995 | Kunz .................... 250/227.21 |
| 5,469,369 A | | 11/1995 | Rose-Pehrsson et al. |
| 5,563,341 A | * | 10/1996 | Fenner et al. ............ 73/335.11 |
| 5,646,336 A | | 7/1997 | Thompson et al. |
| 5,693,538 A | | 12/1997 | Capuano et al. |
| 5,719,323 A | * | 2/1998 | Ellzy ......................... 73/23.41 |
| 5,744,902 A | | 4/1998 | Vig |
| 5,801,297 A | * | 9/1998 | Mifsud et al. ............. 73/23.34 |
| 5,959,191 A | | 9/1999 | Lewis et al. |
| 5,959,297 A | | 9/1999 | Weinberg et al. |
| 5,970,803 A | | 10/1999 | Staples et al. |
| 6,360,585 B1 | * | 3/2002 | Potyrailo et al. ............. 422/83 |
| 6,438,497 B1 | * | 8/2002 | Mansky et al. ............... 702/22 |
| 6,450,008 B1 | * | 9/2002 | Sunshine et al. .......... 73/23.34 |
| 6,534,319 B1 | * | 3/2003 | Liu ............................ 436/151 |

FOREIGN PATENT DOCUMENTS

| | | |
|---|---|---|
| WO | WO 96/42011 | 12/1996 |
| WO | WO 97/32208 | 9/1997 |
| WO | WO 99/18431 | 4/1999 |

OTHER PUBLICATIONS

Barisci, Joseph N. "Development of an Electronic Nose" Proceedings of SPIE.—The international Society of Optical Engineering, 3242, pp. 164–171 (1997).*

Musio, Fernando "Low Frequency A.C. response of Polypyrrole Gas Sensors", Sensors & Actuators, pp. 97–103, (1997).*

Armani, M.E. "Multi–frequency measurments of organice conducting polmers for sensing of gases and vapors", Sensors and Actuators, pp. 137–141, (1996).*

(Continued)

Primary Examiner—Jill Warden
Assistant Examiner—Monique T. Cole
(74) Attorney, Agent, or Firm—Cantor Colburn LLP

(57) ABSTRACT

In one embodiment, the present method includes the steps of introducing a volume of a sample into a vapor delivery line and volatilizing at least a portion of the volume as it is carried through the vapor delivery line. At least a portion of the volatilized volume contacts a sensor element, which produces a signal that is monitored to reveal information about the sample. All components upstream of the sensor element are substantially free of sorbent materials so that the sample volume does not contact a substantially sorbent material before contacting the sensor element.

25 Claims, 6 Drawing Sheets

OTHER PUBLICATIONS

Sigman, MS; Jacobsen, EN, Schiff Base Catalysts for the Asymmetric Strecker Reaction Identified and Optimized From Parallel Synthetic Libraries, *J. Am. Chem. Society*, 1998, 120, 4901–4902.

Newcomb, WS, Deegan, TL, Miller, W., Porco, Jr., JA, Analysis of 9–Fluorenylmethoxycarbonyl (FMOC) Loading of Solid–Phase Synthesis resins by Gas Chromatography, *Biotechnol. Bioeng. (Comb. Chem.)*, 1998, 61, 55–60.

Shaughnessy, KH, Kim, P., Hartwig, JF, A Fluorescence–Based Assay for High–Throughput Screening of Coupling Reactions. Application to heck Chemistry., *J. Am. Chem. Society*, 1999, 121, 2123–2132.

Newsam, JM, Schuth, F., Combinatorial Approaches As a Component of High–Throughput Experimentation (THE) in Catalysis Research, *Biotechnol. Bioeng. (Comb. Chem.)*, 1998/1999, 61, 203–216.

Zellers, ET, Park, J., Hsu, T., Groves, WA, Establishing a Limit of Recognition for a Vapor Sensor Array, *Anal. Chem.*, 1998, 70, 4191–4201.

Hierlemann, A., Schweizer–Berberich, M. Weimar, U., Kraus, G., Pfau, A., Gopel, W., Pattern Recognition and Multicomponent Analysis, *In Sensors Update*, vol. 2, 1996, 119–180.

Gardner, JW, Hines, EL, *In Handbook of Biosensors and Electronic Noses. Medicine, Food, and the Environment*, Pattern Analysis Techniques, 1997, 633–652.

Beebe, KR, Pell, RJ, Seasholtz, JBM, *Chemometrics: A Practical Guide*, Chapter 2, 1998, 81–110.

Park, J., Groves, WA, Zellers, ET, Vapor Recognition With Small Arrays of Polymer–Coated Microsensors. A Comprehensive Analysis, *Anal. Chem.* 1999, 71, 3877–3886.

Michael, KL, Taylor, LC, Schultz, SL, Walt, DR, Randomly Ordered Addressable High–Density Optical Sensor Arrays, *Anal. Chem.*, 1998, 70, 1242–1248.

Dickinson, TA, Michael, KL, Kauer, JS, Walt, DR. Convergent, Self–Encoded Bead Sensor Arrays in the Design of an Artificial Nose, *Anal. Chem.*, 1999, 71, 2192–2198.

Furuki, M., Pu, LS, Hybrid Gas Detector of Squarylium Dye Langmuir–Blodgett Film Deposited on a Quartz Oscillator, *Thin Solid Films*, 1992, 210/211, 471–473.

Furuki, M., Pu, LS, Gas Detection By A Multi–Hybrid Sensor With Dye Langmuir–Blodgett Films Deposited on a Quartz Oscillator, *Mol. Cryst. Liq. Cryst.*, 1993, 227, 325–337.

Hierlemann, A., Ricco, AJ, Bodenhofer, K. Gopel, W., Effective use of Molecular Recognition in Gas Sensing: Results From Acoustic Wave and In Situ FT–IR Measurements, *Anal. Chem.*, 1999, 71, 3022–3035.

Thomas, RC, Hierlemann, A., Staton, AW, Hill, M., Ricco, AJ, Reflectance infrared Spectroscopy On Operating Surface Acoustic Wave Chemical Sensors During Exposure to Gas–Phase Analytes, *Anal. Chem.*, 1999, 71, 3615–3621.

Snow, AW, Barger, WR, Klusty, M., Simultaneous Electrical Conductivity and Piezoelectric Mass Measurements On Iodine–Doped Phthalocyanine Langmuir–Blodgett Films, *Langmuir*, 1986, 2, 513–519.

Harsanyi, G., Sensor Structures With Sensitive Polymers, *Polymer Films in Sensor Applications*, Chapter 2, 1995, 53–92.

Potyrailo, RA, Hobbs, SE, Hieftje, GM, Optical Waveguide Sensors in Analytical Chemistry: Today's Instrumentation, Applications and Trends for Future Development, *Anal. Chem.*, 1998, 362, 349–373.

Grate, JW, Abraham, MH, McGill, RA, Sorbent Polymer Materials for Chemical Sensors and Arrays, *In Handbook of Biosensors and Electronic Noses. Medicine, Food, and the Environment*, 1997, 593–612.

Kindlund, A. Sundgren, H. Lundstrom, I., Quartz Crystal Gas Monitor With A Gas Concentrating Stage, *Sens. Actuators*, 1984, 6, 1–17.

Shaffer, RE, Rose–Pehrsson, SL, McGill, RA, Multiway Analysis of Preconcentrator–Sampled Surface Acoustic Wave Chemical Sensor Array Data, *Field Analyt. Chem. Technol.*, 1998, 2, 179–192.

Groves, WA, Zellers, ET, Frye, GC, Analyzing Organic Vapors In Exhaled Breath Using A Surface Acoustic Wave Sensor Array With Preconcentration: Selection and Characterization of the Preconcentrator Absorbent, *Anal. Chim. Acta*, 1998, 371, 131–143.

Grate, JW, Rose–Pehrsson, SL, Venezky, DL, Klusty, M. Wohltjen, H., Smart Sensor System For Trace Organophosphorus and Organosulfur Vapor Detection Employing a Temperature–Controlled Array of Surface Acoustic Wave Sensors, Automated Sample Preconcentration, and Pattern Recognition, *Anal. Chem.*, 1993, 65, 1868–1881.

Groves, WA, Zellers, ET, Prototype Instrument Employing a Microsensor Array for the Analysis of Organic Vapors in Exhaled Breath, *Am. Ind. Hyg. Assos. J.*, 1996, 57, 1103–1108.

\* cited by examiner cresol - circles; benzoquinone - crosses

METHOD AND APPARATUS FOR RAPID SCREENING OF VOLATILES

BACKGROUND OF THE INVENTION

1. Field of the Invention

The present invention is directed to a method and apparatus for rapid screening of volatiles in reaction products and, more specifically, to a method and apparatus for rapid screening of volatiles in complex combinatorial libraries.

2. Discussion of Related Art

Since its introduction in 1970, combinatorial chemistry has become a popular research tool among scientists in many fields. Combinatorial screening for biological activity has been prevalent in the pharmaceutical industry for nearly twenty years. Recently, combinatorial screening of catalysts for the chemical and materials industries has been developed and continues to be an attractive research method.

One of the many challenges in the development of combinatorial screening for production scale reactions is the difficulty involved in emulating production scale behavior at the micro-scale necessary for combinatorial work. Furthermore, rapid analytical techniques capable of measuring both the semi-quantitative and qualitative properties necessary for high throughput screening of combinatorial libraries continue to elude the industry. For example, high throughput screening of volatiles in complex combinatorial libraries presents unique problems for practitioners.

Traditional analysis methods for volatile species involve gas chromatography (GC), mass spectrometry (MS), GC/MS, and various spectroscopic techniques. The use of chemical sensors is an appealing alternative for detection of volatiles. In particular, chemical sensors potentially afford many attractive features for screening of combinatorial libraries such as ruggedness, small size, high sensitivity, and low cost. However, a single sensor often suffers from a non-specific response, making the identification and quantitation of species problematic. To address this issue, conventional chemical sensors have being utilized in combination with one another to form an array of sensors. The number of sensors in the array typically range from less than ten to thousands depending on the type of sensor response, complexity of analyzed mixture, concentration of each vapor component, signal and noise levels produced by each sensor, similarity of the vapor response patterns, and other factors.

Efforts to reduce the number of transducers in sensor arrays have been directed to measuring multiple parameters from a single sensing element. Although measurement of dual responses from a single sensing device ostensibly provides twice as much information as a single output sensor, this detection approach has traditionally exhibited several limitations, including the following:

1. Data analysis from a dual-response sensor is complicated because it may require multi-way calibration procedures.

2. Further complications can arise from nonlinear sensor response measured by one or both detection methods as a function of concentration of multiple analytes.

3. Information from a single sensor that operates in a dual-response mode is obtained at the cost of complication of the sensor design and reduction of its robustness.

4. Further increase of information content of such a sensor becomes problematic because it requires yet another measurement technique.

5. In a single sensor that operates in a dual-response mode, it is difficult to implement adequate signal referencing strategies for both detection methods.

As the demand for high performance materials continues to grow, new and improved methods of providing products more economically are needed to supply the market. In this context, various reactant and catalyst combinations are constantly being evaluated; however, methods for quickly and accurately determining the identities of chemically or economically superior reactant systems for industrial processes continue to challenge the industry. New and improved methods and devices are needed for rapid screening of potential reactant systems and catalysts.

SUMMARY OF THE INVENTION

Accordingly, the present invention is directed to a method and apparatus that is capable of rapidly screening volatiles in complex, multi-component samples. In one embodiment, the present method includes the steps of introducing a volume of a sample into a vapor delivery line and volatilizing at least a portion of the volume as it is carried through the vapor delivery line. At least a portion of the volatilized volume contacts a sensor element, which produces a signal that is monitored to reveal information about the sample. The method is adaptable to high throughput screening because, inter alia, the sample volume does not contact a substantially sorbent material before contacting the sensor element.

Another aspect of the present invention is directed to an apparatus which includes an injector; a vapor delivery line in fluid communication with the injector; and a sensor element in fluid communication with the vapor delivery line and positioned downstream of both the injector and the vapor delivery line. All components upstream of the sensor element are substantially free of sorbent material. A monitor is placed in communication with the sensor element to measure a property of the sample.

BRIEF DESCRIPTION OF THE DRAWINGS

Various features, aspects, and advantages of the present invention will become more apparent with reference to the following description, appended claims, and accompanying drawings, wherein

DETAILED DESCRIPTION OF PREFERRED EMBODIMENTS

Figure 1:
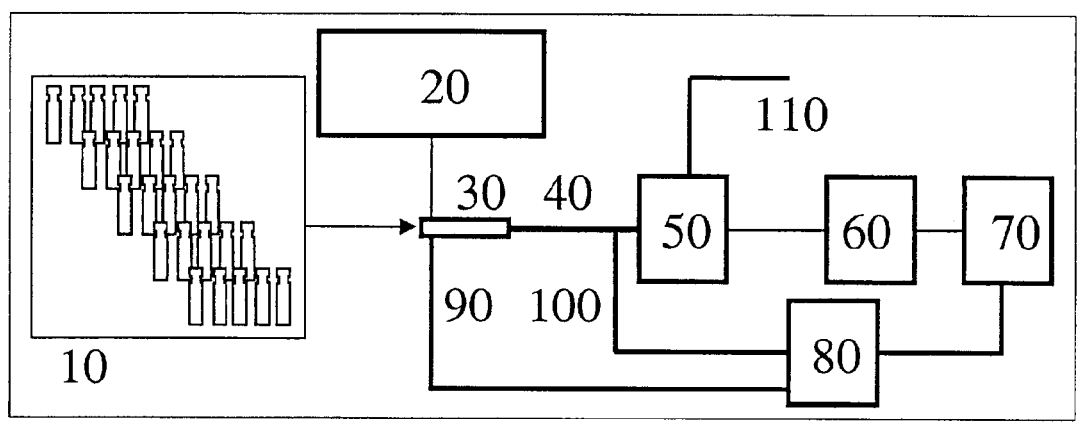
FIG. 1 is a schematic view of various aspects of an embodiment of the present invention.

Terms used herein are employed in their accepted sense or are defined. In this context, the present invention is directed to a method and apparatus for rapidly screening volatiles, especially in complex, multi-component samples. The present method and apparatus employs chemical sensors to obtain qualitative and quantitative information about sample components. However, unlike conventional sensor systems, the present system does not employ a sorbing material upstream of the sensor element, thereby overcoming a multitude of the aforementioned shortcomings presented by conventional systems and allowing for both high throughput screening and miniaturization.

In an exemplary embodiment, the method includes the steps of introducing a volume of a sample into a vapor delivery line and volatilizing at least a portion of the sample volume as it is carried through the vapor delivery line. At least a portion of the volatilized sample is brought into contact with a sensor element, which produces a signal that is monitored to produce data relating to the sample. It is noted that the sample volume does not contact a substantially sorbent material before contacting the sensor element.

As used herein, the term "substantially sorbent material" includes materials that are typically used as either a stationary phase in a gas chromatography column or as collector material in a preconcentrator. Substantially sorbent materials retard or prevent movement of one or more volatile species through adsorption, absorption, ion exchange, ion exclusion, ion retardation, chemisorption, dialysis, or the like such that sample components either do not pass through an area (at a given temperature) or pass through the area at differing rates. In particular, the vapor delivery line of the present invention does not contain a material that is substantially sorbent within the operating temperature range of the present method, thereby allowing volatile sample components to pass substantially freely through the vapor delivery line to the sensor.

Preferred embodiments of the present method employ a combination of (1) periodic introduction of a volatile containing sample into an apparatus; (2) evaporation of volatile components in the sample; and (3) measurement of a generated vapor pulse by a sensing device. In these embodiments, the detection concept involves temporal modulation of the concentration of analyte vapor and measurement of both the temporal profile of the sensor response and the magnitude of the signal change at a given time. This approach allows for a reduction of the number of sensor elements necessary for effective monitoring. Data handling is simplified because both types of information (qualitative and quantitative) about the analytes are provided in the temporally modulated sensor output. Reduction of the number of sensor elements in a sensor array leads to diminution of the physical size of the array. Upon operation of multiple sensors in parallel, this feature allows for effective analysis of dense combinatorial libraries of materials. This flexibility also allows for miniaturization, with concomitant cost savings and increased usefulness in space-limited applications, such as high throughput screening of combinatorial libraries.

An apparatus capable of performing various embodiments of the present method is schematically shown in FIG. 1, wherein the apparatus can include an auto-injector 20, an injection port 30, a vapor delivery line 40, a sensor array 50, frequency counters 60, a computer 70, flow controllers 80, a carrier stream line 90, a purge stream line 100, and an exit port 110. In operation, auto-injector 20 is capable of introducing a volume of solution from one or more of the samples from a combinatorial library 10 into the apparatus through injection port 30. Various components of the sample are volatilized as they travel through vapor delivery line 40. The length of vapor delivery line 40 is chosen such that substantial amounts of the volatile components evaporate before entering sensor array 50; therefore optimal length of line 40 will vary depending on the volatility of the sample. It is contemplated that volatilization will take place at ambient conditions; however, if desired, an external heating source (e.g., heating coil) can be utilized to aid in sample evaporation in vapor delivery line 40.

The vapors are carried by an inert and/or non-explosive carrier gas (e.g., nitrogen) into sensor array 50 where the volatilized sample components contact the sensor elements. Auto-injector 20, injection port 30, vapor delivery line 40 and sensor array 50 are all in fluid communication with each other such that volatilized sample volumes can freely flow through delivery line 40 to the sensor elements of array 50, which may be, for example, optical, semiconducting, or electrochemical in nature.

The output frequency of each sensor element is monitored by corresponding frequency counters 60 and stored in computer 70. In alternative embodiments, computer 60 can control the flow of the carrier gas through flow controllers 80, which regulate gas flow through both carrier stream line 90 and purge stream line 100. To allow for adequate evaporation upstream of sensor 50, carrier stream flow is preferably between about 1 mL/min and about 1000 mL/min and more preferably between about 150 mL/min and about 500 mL/min. Vapors exit the apparatus through exit port 110.

The sensor elements are typically formed of an oscillating crystal structure (e.g., transducer) which produces measurable frequency variations responsive to certain stimuli. An acceptable crystal structure in certain applications is an AT-cut quartz crystal oscillating in a thickness-shear mode (TSM) and having a fundamental frequency of between about 1 MHz and about 50 MHz.

The sensor elements are preferably coated with a chemically sensitive material to form a chemically sensitive film proximate (i.e., on or near) the surface of the sensor element. A variety of art-recognized materials can be applied to the surfaces of the sensor elements and analyte-coating interactions can be detected using a variety of art-recognized sensing techniques. For example, a large number of vapor-sorbing materials are often used in piezoelectric, optical, and other sensors. Operation of these sensors is based on the interactions of a chemically sensitive film with a vapor while monitoring variations in certain film properties as a function of analyte concentration or concentrations of multiple analytes in a mixture. The measured film property can be a change in mass, viscoelasticity, or other mechanical property, as well as dielectric or optical properties. The optical properties can be altered with an analyte partitioned into the film and can be monitored as the change in the absorbance, scattering, refractive index, luminescence, or the like. A chemically sensitive dye can be incorporated into the bulk of the film or a dye molecule can be directly attached to a molecule of the film. Changes in optical properties of the dye can be indicative of variations in the chemical environment proximate the sensor.

In addition to art-recognized sensor coatings, the sensor elements of the present apparatus can be coated with polymeric films that include hardblock and softblock polymer base structures (referred to herein as "hard-soft block elastomers"). Such films can be formed of, e.g., thermoplastic elastomers, polyether block polyamides, silicone polyimides, and combinations thereof. Acceptable silicone polyimides (sometimes referred to as "silicone polyetherimides") include Siltem® 2000 elastomers (available from the General Electric Company, Pittsfield, Mass.) Acceptable elastomers also include XD-7™ BPA-PC-Silicone 50% dimethylsiloxane (available from the General Electric Company, Pittsfield, Mass.). Additionally, one or more sensor elements of the present apparatus can be coated with an amorphous fluoropolymer, such as random copolymers of tetrafluoroethylene and perfluoro-2,2-dimethyl-1,3-dioxole sold under the trademark Teflon AF (available from Du Pont Corporation, Wilmington, Del.).

These films can be formed in accordance with any art-recognized method for disposing polymer films on sensor substrates, including dip coating, spin coating, spray coating, vapor deposition, laser-assisted deposition, and the like. When an array of sensor elements is used, it can be advantageous to coat various elements with different chemically sensitive materials, each containing different functional groups to provide unique sensor response to the presence of volatile compounds in the sample stream.

The monitor, which can include a frequency counter, is adapted to receive a signal from the sensor elements representing a measured property of the chemically sensitive films. Upon exposure to the analyte stream, the oscillation frequency of each sensor element varies as a function of both the composition of the sample stream and the concentration of the chemical species of interest. A temporally modulated combination of responses from each of the transducers provides a unique signature indicating the presence of certain chemicals. The data produced can be displayed with and/or stored in a computer for analysis.

EXAMPLES

The following examples are provided in order that those skilled in the art will be better able to understand and practice the present invention. These examples are intended to serve as illustrations and not as limitations of the present invention as defined in the claims herein. Unless otherwise noted, all of the following examples employ the apparatus shown generally in FIG. 1 and described supra.

Example 1

For determination of volatile arene oxidation products in combinatorial samples, model mixtures containing varying amounts of toluene, acetonitrile, phenol, benzoquinone, and hydroquinone were prepared as illustrated below in Table 1:

TABLE 1

| Sample | Toluene, mL | Acetonitrile, mL | Cresol, g | Benzoquinone, g | Hydroquinone g |
|---|---|---|---|---|---|
| 0 | 5 | 5 | 0 | 0 | 0 |
| 1 | 5 | 5 | 0.015 | 0 | 0 |
| 2 | 5 | 5 | 0.044 | 0 | 0 |
| 3 | 5 | 5 | 0.0739 | 0 | 0 |
| 4 | 5 | 5 | 0.153 | 0 | 0 |
| 5 | 5 | 5 | 0.1993 | 0 | 0 |
| 6 | 5 | 5 | 0 | 0.0154 | 0 |
| 7 | 5 | 5 | 0 | 0.0387 | 0 |
| 8 | 5 | 5 | 0 | 0.0768 | 0 |
| 9 | 5 | 5 | 0 | 0.1232 | 0 |
| 10 | 5 | 5 | 0 | 0.223 | 0 |
| 11 | 5 | 5 | 0.0473 | 0.0735 | 0 |
| 12 | 5 | 5 | 0.0811 | 0.106 | 0 |
| 13 | 5 | 5 | 0.0966 | 0.1008 | 0 |
| 14 | 5 | 5 | 0.1296 | 0.0339 | 0 |
| 15 | 5 | 5 | 0.0603 | 0.1748 | 0 |
| 16 | 3 | 7 | 0.247 | 0.049 | 0 |
| 17 | 8 | 2 | 0.098 | 0.1202 | 0 |
| 18 | 5 | 5 | 0 | 0 | 0.1137 |
| 19 | 5 | 5 | 0 | 0 | 0.235 |
| 20 | 1 | 9 | 0.0885 | 0 | 0 |
| 21 | 8 | 2 | 0.0993 | 0 | 0 |
| 22 | 2 | 8 | 0.1228 | 0 | 0 |
| 23 | 9 | 1 | 0.1159 | 0 | 0 |
| 24 | 5 | 5 | 0 | 0 | 0.0835 |
| 25 | 5 | 5 | 0 | 0 | 0.175 |

The sensor array included four AT-cut quartz crystals with gold electrodes. These crystals oscillate in TSM with a fundamental frequency of 10 MHz. Three of the crystals were coated with different chemically sensitive materials, and all four were arranged in a low-dead volume flow-through gas cell. The resonant oscillation frequency of each crystal was monitored as a function of time. The identification and thickness of the films are detailed below:

| Sensor Elements in the Array | Coating Material | Film Thickness kHz* |
|---|---|---|
| Sensor 1 | None | 0 |
| Sensor 2 | Hard-soft block elastomer Siltem 2000 | 5 |
| Sensor 3 | Amorphous fluoropolymer Teflon AF 1600 | 13 |
| Sensor 4 | Hard-soft block elastomer BPA-PC-Silicone 50% DMS "XD-7" | 7 |

*measured as the change in oscillation frequency of a 10-MHz crystal upon film deposition.

The flow rate of the nitrogen carrier gas was 500 mL/min. The flow rate of the purge line was 4.5 L/min. The auto-injector sequentially introduced a 2 μL aliquot of each sample mixture into the vapor delivery line. The purge line was operated for 250 s with a 380 s delay after injection of a sample volume into the system.

Figure 2:
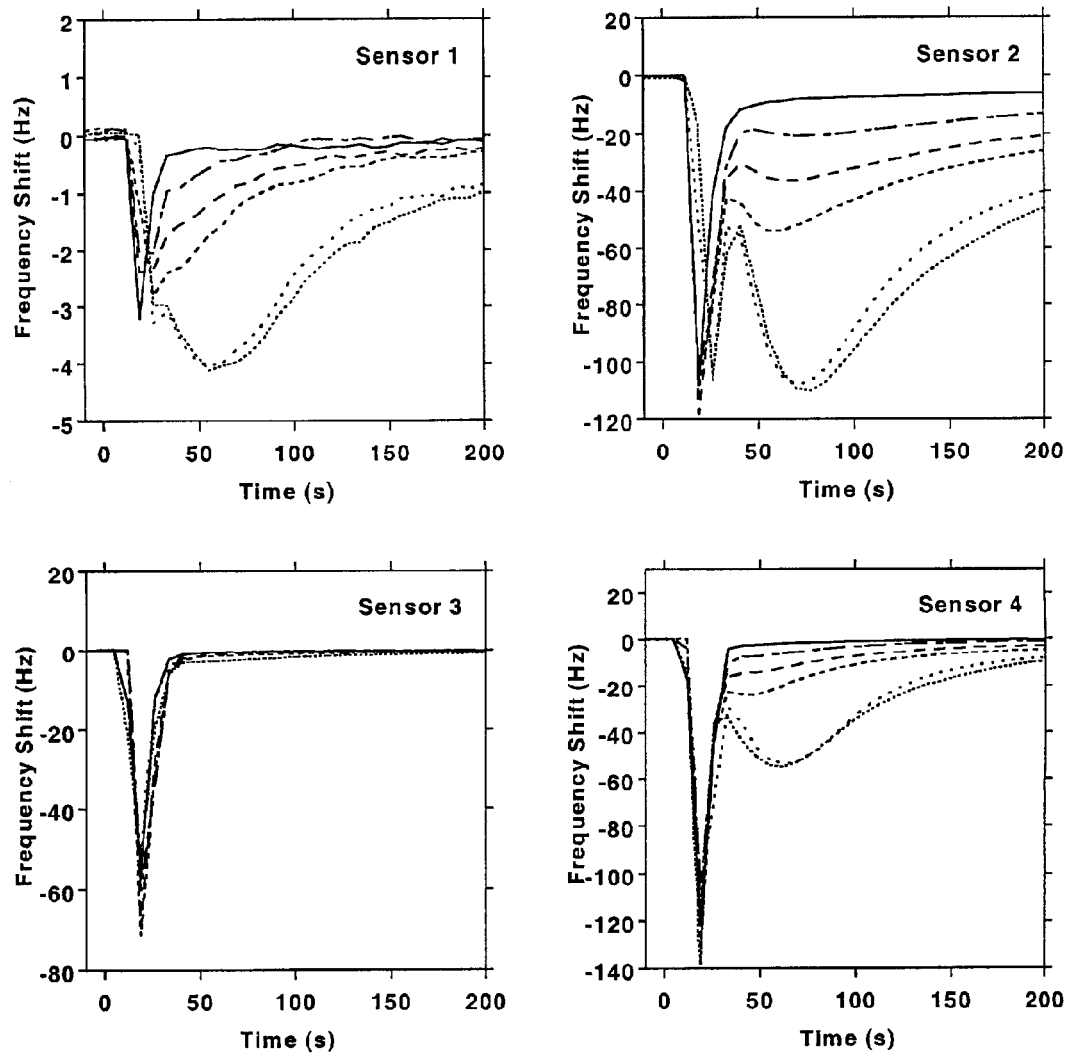
FIG. 2 is a graphical representation of data obtained from an aspect of an embodiment of the present invention.

The time dependent frequency changes of each sensor in the sensor array upon introduction of samples with different amounts of cresol are illustrated in FIG. 2. The data demonstrate that each sensor can be useful for detecting certain analytes. Specifically, sensor 1 can be useful for analysis of analytes with high boiling temperatures approximately 50 s after sample injection. Sensor 2 can be useful for analysis of analytes having both low and high boiling temperatures approximately 20 and 50 s after sample injection, respectively. Sensor 3 can be useful for analysis of analytes with low boiling temperatures approximately 20 s after sample injection. Sensor 4 can be useful for analysis of analytes having both low and high boiling temperatures approximately 20 and 50 s after sample injection, respectively. With the conditions used, the highest sensitivity for analysis of low boiling temperature analytes was provided by sensor 4, where the maximum signal change for these types of analytes was about 140 Hz. The highest sensitivity for analysis of high boiling temperature analytes was provided by sensor 2, where the maximum signal change for these types of analytes was about 110 Hz.

Figure 3:
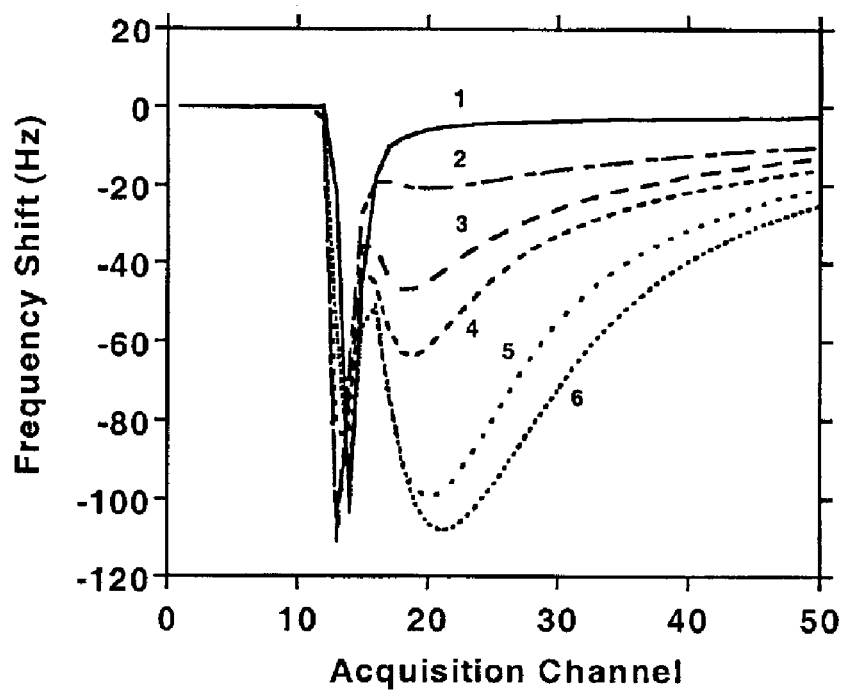
FIG. 3 is a graphical representation of data obtained from an aspect of an embodiment of the present invention.
Figure 4:
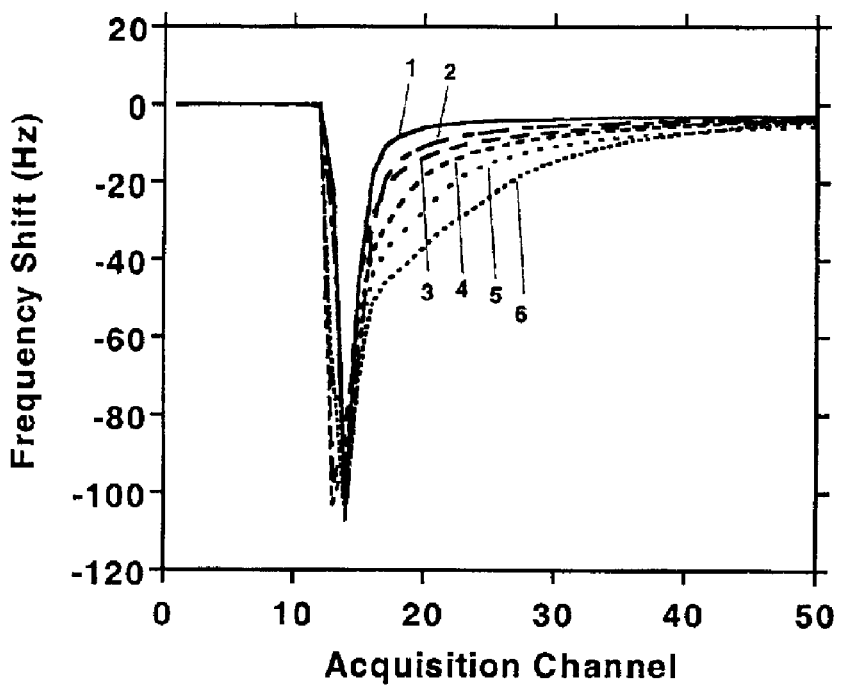
FIG. 4 is a graphical representation of data obtained from an aspect of an embodiment of the present invention.

Because it showed high sensitivity to arene oxidation products, sensor 2 was utilized to evaluate the discrimination ability of time-modulated detection for identification and quantitation of cresol and benzoquinone. FIG. 3 depicts the temporal response of sensor 2 to increasing amounts of cresol in injected samples. Numbers 1–6 indicate cresol amounts of 0, 3, 8.8, 14.8, 30.6, and 40.0 µg respectively. FIG. 4 depicts the temporal response of sensor 2 to increasing amounts of benzoquinone in injected samples. Numbers 1–6 indicate benzoquinone amounts of 0, 3.1, 7.7, 15.4, 24.6, and 44.6 µg respectively. Each acquisition channel in FIG. 3 and FIG. 4 corresponds to 7.25 s.

Figure 5:
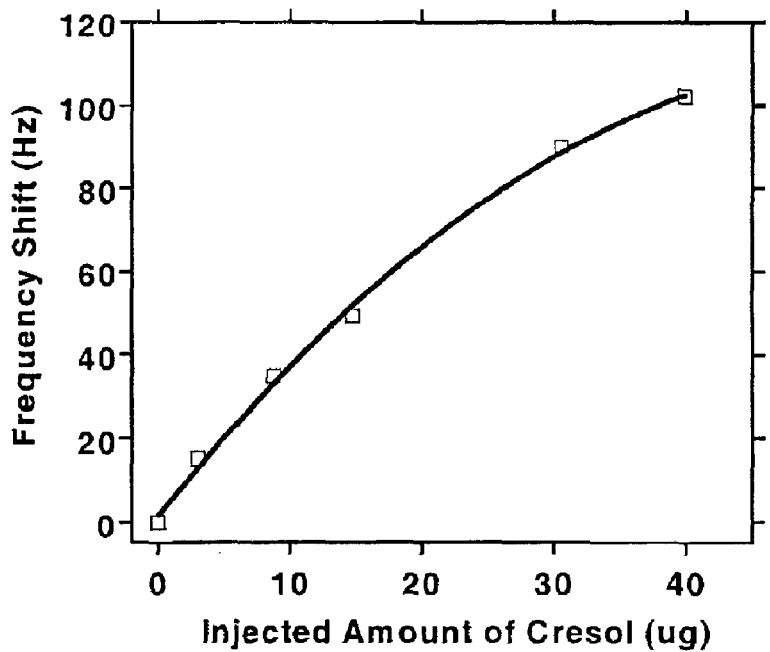
FIG. 5 is a calibration plot useful in carrying out an aspect of an embodiment of the present invention.
Figure 6:
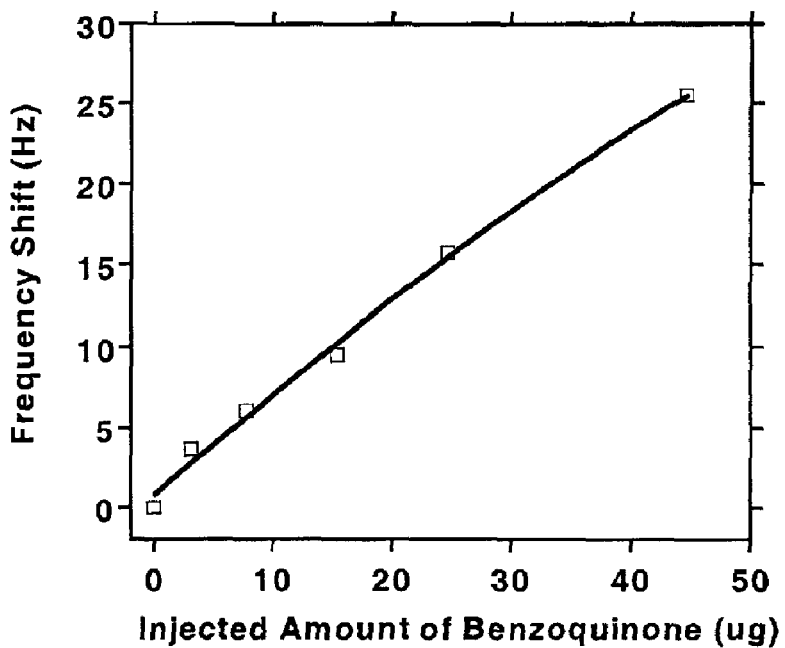
FIG. 6 is a calibration plot useful in carrying out an aspect of an embodiment of the present invention.

Calibration plots for determination of cresol and benzoquinone with a single sensor are presented in FIGS. 5 and 6, respectively. They were constructed by plotting the frequency shift of sensor 2 measured 72 s after injection as a function of analyte concentration for each of the samples.

Example 2

Figure 7:
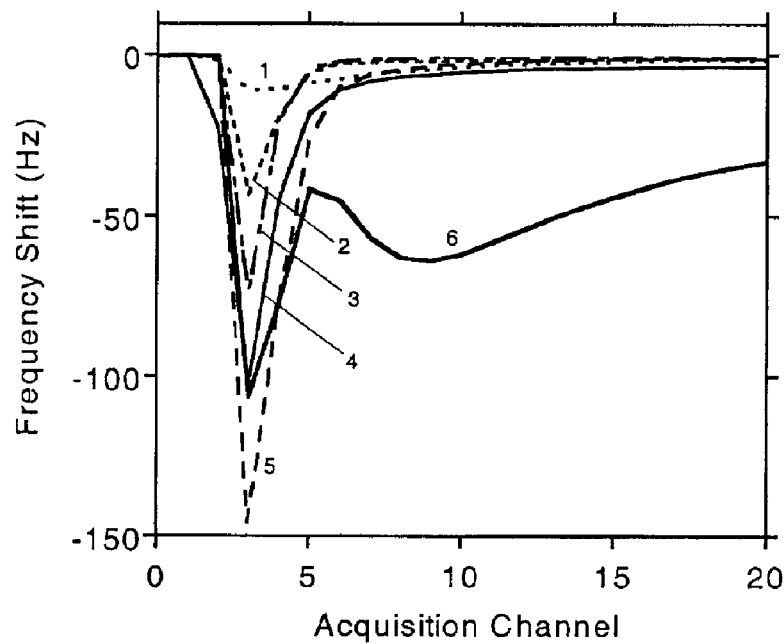
FIG. 7 is a graphical representation of data obtained from an aspect of an embodiment of the present invention.

To show the present method and apparatus's effectiveness in identifying and quantifying volatile components in complex mixtures, the general process of Example 1 was repeated with a single sensor coated with a Siltem® 2000 polymer film. The disclosed apparatus and method of temporal modulation of analyte concentrations permits selective determination of arene oxidation products in complex mixtures. For example, injection of pure solvents such as benzene, toluene, acetonitrile, water, and their mixtures do not produce any interference with the measurements of arene oxidation products. Exemplary data showing the excellent selectivity of the sensor coated with a Siltem® 2000 polymer film are presented in FIG. 7, where lines 1–6 represent injected samples of water, acetonitrile, benzene, toluene: acetonitrile solution—1:1, toluene alone, and sample #3 from Table 1, respectively. Furthermore, addition of hydroquinone to solutions (see Table 1) did not alter sensor response, thereby demonstrating that the sensor is substantially immune to this interference.

Selective determination of cresol and benzoquinone in complex mixtures was achieved with a single sensor coated with a Siltem® 2000 polymer film. Referring again to Table 1, samples 0–10 were used to construct the sensor calibration model, and samples 11–17 were used as the validation set. The model was constructed using a method of locally weighted regression (LWR) available, for example, in PLS_Toolbox™ software (Version 2.0, available from Eigenvector Research, Inc., Manson, Wash.) operated with Matlab™ software (Version 5.3, available from The Mathworks Inc., Natick, Mass.). In the LWR method, local regression models were produced using points that were near the sample to be predicted in independent variable space. Furthermore, each calibration sample was weighted in the regression according to how close it was to the sample to be predicted. This method is especially useful for modeling of non-linear systems. The coated sensor is one such system because of its non-linear response as a function of analyte concentration (see FIG. 5).

For selective determination and quantitation of cresol and benzoquinone in complex mixtures, data collected with the sensor were preprocessed before constructing the calibration model and its validation. The preprocessing involved taking the first derivative of the temporal profiles to improve the reproducibility. For analysis, a time window between 50 and 150 s. after sample injection was utilized.

Figure 8:
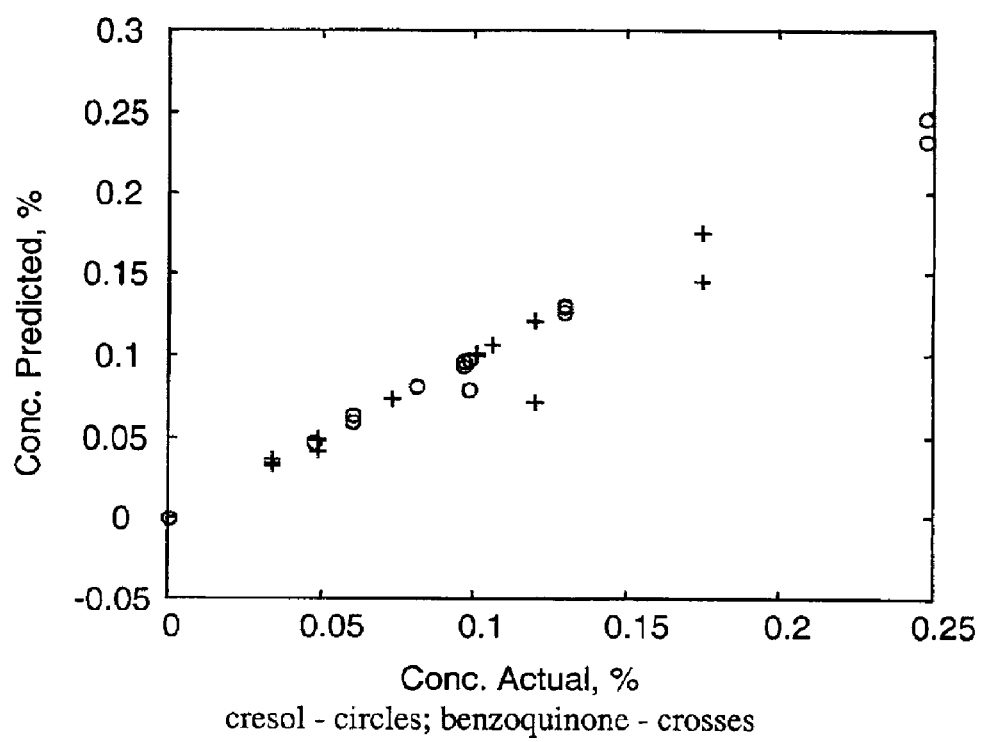
FIG. 8 is a correlation plot showing the effectiveness of an embodiment of the present invention.

The validation plot between actual and predicted concentrations of cresol and benzoquinone in complex mixtures (samples 11–17 of Table 1) is presented in FIG. 8.

Example 3

To assess the speed of analysis using the disclosed method and apparatus, several samples containing phenol as an arene oxidation product were prepared as described in Table 2 below:

TABLE 2

| Sample # | Benzene, mL | Acetonitrile, mL | Phenol, g |
|---|---|---|---|
| 1 | 5 | 5 | 0 |
| 2 | 5 | 5 | 0.0209 |
| 3 | 5 | 5 | 0.0956 |
| 4 | 5 | 5 | 0.1624 |
| 5 | 5 | 5 | 0.2041 |
| 6 | 5 | 5 | 0.3397 |
| 7 | 5 | 5 | 0.7132 |

Measurements were performed with a sensor coated with a Siltem® 2000 polymer film. The flow rate of the carrier gas was 500 mL/min. The flow of the purging line was 5 L/min. The purge line was operated for 90 s with a 150 s delay after injection of the sample into the system. It is noted that the duration of purge line operation can be easily decreased by using a higher purging flow. The minimum time delay period was limited by the requirements to rinse the injector and to purge the sensor.

Figure 9:
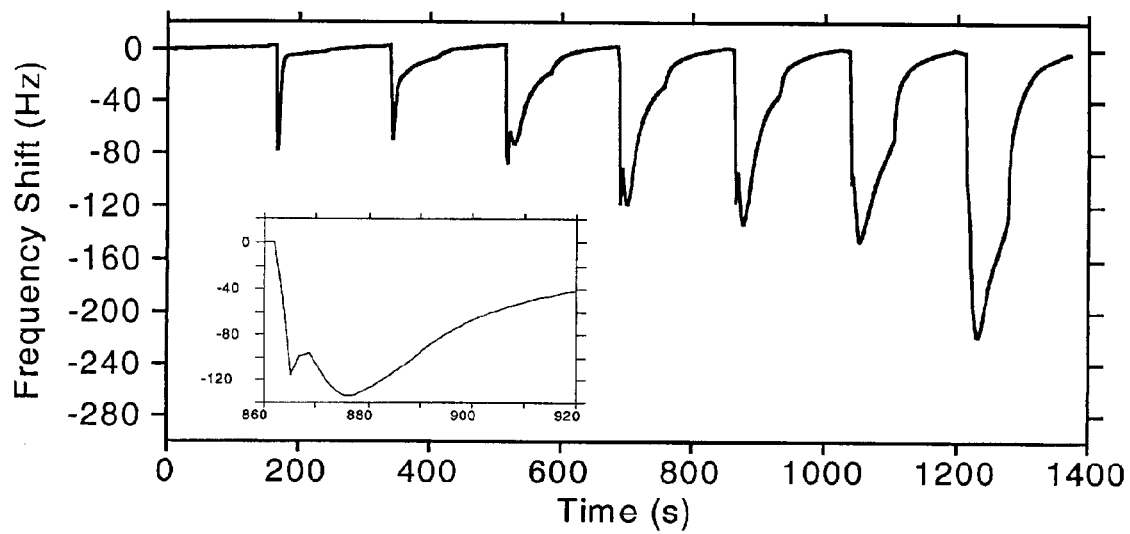
FIG. 9 is a graphical representation of data obtained from an embodiment of the present invention.

Data presented in FIG. 9 demonstrate that, at the conditions used, maximum sensor response from the phenol component was observed 10 s after sample injection. Measurements of volatile arene oxidation products in complex samples were accomplished within 30 s after injection of the sample into the sensor. The inset of FIG. 9 shows rapid sensor response from 860 to 920 s.

It will be understood that each of the elements described above, or two or more together, may also find utility in applications differing from the types described herein. While the invention has been illustrated and described as embodied in a method and apparatus for rapid screening of volatiles, it is not intended to be limited to the details shown, since various modifications and substitutions can be made without departing in any way from the spirit of the present invention. For example, additional analytical techniques can be used in concert with the present system when needed. As such, further modifications and equivalents of the invention herein disclosed may occur to persons skilled in the art using no more than routine experimentation, and all such modifications and equivalents are believed to be within the spirit and scope invention as defined by the following claims.

What is claimed is:

1. A method for rapidly screening volatile substances in a sample, said method comprising the steps of:
    a) introducing a volume of said sample into a vapor delivery line;
    b) volatilizing at least a portion of said volume as said volume is carried through said vapor delivery line;
    c) contacting at least a portion of said volatilized with a sensor element, wherein the sensor element is coated with a hard-soft block elastomer; and, wherein said volume does not contact a substantially sorbent material before contacting said sensor element; and
    d) monitoring a signal from said sensor element,
wherein said signal comprises a response of said sensor element to a temporally-determined variation in a concentration of said vapor proximate said sensor element, and wherein said signal is capable of providing both qualitative and quantitative information about said volatile substances in said sample.

2. The method of claim 1, wherein said sensor element is an optical sensor element.

3. The method of claim 1, wherein said sensor element is an electrochemical sensor element.

4. The method of claim 1, wherein said sensor element comprises a semiconductor.

5. The method of claim 1, wherein said sensor element comprises a quartz crystal.

6. The method of claim 1, wherein the hard-soft block elastomer comprises a silicone polyimide.

7. The method of claim 1, wherein said hard-soft block elastomer comprises a block dimethylsiloxane-carbonate copolymer.

8. The method of claim 1, wherein step c) comprises contacting at least a portion of said volatilized volume with an array of sensor elements.

9. The method of claim 1, wherein said volume is carried through said vapor delivery line by an inert carrier gas.

10. The method of claim 9, wherein said inert carrier gas is flowing through said vapor delivery line at a rate of between about 1 mL/min and about 1000 mL/min.

11. The method of claim 10, wherein said inert carrier gas is flowing through said vapor delivery line at a rate of between about 150 mL/min and about 500 mL/min.

12. The method of claim 1, wherein said signal from said sensor element is monitored as a function of time.

13. The method of claim 12, wherein said signal is monitored with at least one frequency counter to produce data.

14. The method of claim 13, wherein said data are stored in a computer.

15. The method of claim 9, further comprising the step of controlling the flow of said inert carrier gas through said vapor delivery line with flow controllers in communication with a computer.

16. A method for rapidly screening volatile substances in a simple, said method comprising the steps of:
   a) introducing a volume of said sample into a vapor delivery line;
   b) volatilizing at least a portion of said volume as said volume is carried through said vapor delivery line;
   c) contacting at least a portion of said volatilized volume with a sensor element comprising a quartz crystal and a chemically sensitive film proximate the surface of said crystal, wherein the chemically sensitive film comprises a hard-soft block elastomer; and wherein said volume does not contact a substantially sorbent material before contacting said sensor element; and
   d) monitoring a measured property of said chemically sensitive film as a function of time to yield both qualitative and quantitative information about said volatile substances in said sample.

17. A method for rapidly screening volatile substances in a sample, the method comprising the steps of:
   (a) introducing a volume of said sample into a vapor delivery line;
   (b) volatilizing at least a portion of said volume as said volume is carried through said vapor delivery line;
   (c) contacting at least a portion of said volatilized volume with a sensor element, wherein the sensor element is coated with a hard-soft block elastomer; and wherein said volume does not contact a substantially sorbent material before contacting said sensor element; and
   (d) monitoring a signal from said sensor element as a function of time to yield both qualitative and quantitative information about said volatile substances in said sample.

18. The method of claim 17, wherein said volume is carried through said vapor delivery line by an analyte-free carrier gas.

19. The method of claim 18, further comprising the step of controlling the flow of said analyte-free carrier through said vapor delivery line with flow controllers in communication with a computer.

20. The method of claim 17, further comprising purging the system to remove any remaining analyte vapors prior to introduction of a second sample into said vapor delivery line.

21. The method of claim 17, wherein the sensor element is coated with a chemically sensitive material to form a chemically sensitive film proximate the surface of the sensor element.

22. The method of claim 17, wherein said sensor comprises a quartz crystal.

23. The method of claim 17, wherein step (c) comprises contacting at least a portion of said volatilized volume with an array of sensor elements.

24. The method of claim 17, wherein said sensor element is an optical element.

25. The method of claim 17, wherein said sensor element is an electrochemical element.

* * * * *

UNITED STATES PATENT AND TRADEMARK OFFICE
CERTIFICATE OF CORRECTION

PATENT NO. : 6,881,585 B1  
APPLICATION NO. : 09/519330  
DATED : April 19, 2005  
INVENTOR(S) : Potyrailo et al.

It is certified that error appears in the above-identified patent and that said Letters Patent is hereby corrected as shown below:

<u>Column 4</u>:
Line 19, after "computer" delete "60" and insert therefor -- 70 --

<u>Column 6</u>:
Line 23, insert therefor -- TABLE 2 --

<u>Column 8</u>:
Line 2, before "below" delete "2" and insert therefor -- 3 --
Line 4, delete "TABLE 2" and insert therefor -- TABLE 3 --
Line 44, after "scope" insert therefor -- of the --
Line 52, after "volatilized" insert therefor -- volume --

Signed and Sealed this

Eighteenth Day of September, 2007

JON W. DUDAS
*Director of the United States Patent and Trademark Office*